(12) United States Patent
Kishimoto et al.

(10) Patent No.: US 11,735,292 B2
(45) Date of Patent: Aug. 22, 2023

(54) INTELLIGENT PERSONALIZED CHEMICAL SYNTHESIS PLANNING

(71) Applicant: INTERNATIONAL BUSINESS MACHINES CORPORATION, Armonk, NY (US)

(72) Inventors: Akihiro Kishimoto, Castleknock (IE); Adi I. Botea, Dublin (IE); Beat Buesser, Ashtown (IE); Bei Chen, Blanchardstown (IE); Takahiko Koyama, Scarsdale, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1384 days.

(21) Appl. No.: 16/057,673

(22) Filed: Aug. 7, 2018

(65) Prior Publication Data
US 2020/0050947 A1 Feb. 13, 2020

(51) Int. Cl.
*G16C 20/10* (2019.01)
*G06F 17/13* (2006.01)
*G06N 5/025* (2023.01)
*G06F 16/903* (2019.01)

(52) U.S. Cl.
CPC ....... *G16C 20/10* (2019.02); *G06F 16/90335* (2019.01); *G06N 5/025* (2013.01); *G06F 17/13* (2013.01)

(58) Field of Classification Search
CPC ........ G16C 20/10; G16C 20/00; G16C 20/70; G16C 20/90; G06F 16/90335; G06F 17/13; G06F 17/11; G06F 17/10; G06F 17/00; G06N 5/025; G06N 3/02; H04L 67/10
See application file for complete search history.

(56) References Cited

U.S. PATENT DOCUMENTS

| 5,862,514 A | 1/1999 | Huse et al. |
| 6,571,226 B1 | 5/2003 | Mydlowec et al. |
| 7,250,950 B2 | 7/2007 | Smith et al. |

(Continued)

FOREIGN PATENT DOCUMENTS

| CN | 103224436 A | 7/2013 |
| CN | 103265420 A | 8/2013 |
| CN | 104355388 A | 2/2015 |

OTHER PUBLICATIONS

Coley et al., "Machine Learning in Computer-Aided Synthesis Planning", 2018 American Chemical Society, pp. 1281-1289. (Year: 2018).*

(Continued)

*Primary Examiner* — Mohamed Charioui
(74) *Attorney, Agent, or Firm* — Griffiths & Seaton PLLC (57) ABSTRACT

Embodiments for intelligent discovery of preferred chemical reaction pathways to a synthesized target compound by a processor. Target compound data of a target compound a user intends to synthesize may be received. A preference score for one or more chemical reaction pathways to the target compound may be calculated based on one or more chemical reactions. One or more preferred chemical reaction pathways to the targeted compound may be determined using a modified retrosynthetic analysis according to the preference score for one or more chemical reactions.

14 Claims, 7 Drawing Sheets

(56) References Cited

U.S. PATENT DOCUMENTS

| | | | | |
|---|---|---|---|---|
| 2002/0077757 A1* | 6/2002 | Bunin | ............ | G16C 20/90 |
| | | | | 702/32 |
| 2002/0099526 A1 | 7/2002 | Patterson et al. | | |
| 2004/0003000 A1* | 1/2004 | Smith | ............ | G16C 20/10 |
| 2005/0124002 A1 | 6/2005 | Cardozo et al. | | |
| 2016/0196323 A1* | 7/2016 | Kim | ............ | G16C 20/10 |
| | | | | 707/737 |
| 2017/0121852 A1* | 5/2017 | Siva Kimar | ............ | G16C 20/60 |

OTHER PUBLICATIONS

Selger et al., "Learning to Plan Chemical Syntheses", arXiv, pp. 1-19 (Year: 2017).*

* cited by examiner

INTELLIGENT PERSONALIZED CHEMICAL SYNTHESIS PLANNING

BACKGROUND OF THE INVENTION

Field of the Invention

The present invention relates in general to computing systems, and more particularly, to various embodiments for recommending to a user at least one personalized chemical reaction pathway to synthesize a target compound by a processor.

Description of the Related Art

Computing systems may be found in the workplace, at home, or at school. Due to the recent advancement of information technology and the growing popularity of the Internet, a wide variety of computer systems have been used in machine learning. Due to the recent advancement of information technology and the growing popularity of the Internet, a wide variety of computer systems have been used in machine learning. Machine learning is a form of artificial intelligence that is employed to allow computers to evolve behaviors based on empirical data.

SUMMARY OF THE INVENTION

Various embodiments for intelligent discovery of preferred chemical reaction pathways to a synthesized target compound using one or more processors are provided. In one embodiment, by way of example only, a method for recommending to a user at least one personalized chemical reaction pathway to synthesize a target molecule, again by a processor, is provided. Target compound data of a target compound a user intends to synthesize may be received. A preference score for one or more chemical reaction pathways to the target compound may be calculated based on one or more chemical reactions. One or more preferred chemical reaction pathways to the targeted compound may be determined using a modified retrosynthetic analysis according to the preference score for one or more chemical reactions.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE DRAWINGS

The present invention relates in general to recommending at least one personalized chemical reaction pathway for targeted chemical compound synthesis. More specifically, the present invention relates to an efficient retrosynthesis analysis system and computer-implemented method for intelligent discovery of preferred chemical reaction pathways to a synthesized target compound.

Discovering pathways to create new chemical compounds play an important role in the pharmaceutical, chemical, food, material and other industries. These pathways are conventionally discovered manually by chemists using techniques such as, for example, retrosynthetic analysis. Retrosynthetic analysis involves the transformation of a target compound into progressively simpler and/or commercially available precursor compounds without any assumptions regarding starting materials (e.g., in-house availability, lead time and quality of supplier). That is, retrosynthetic analysis may identify or discover a new synthesis reaction pathway to a target compound (e.g., molecule, material, etc.) where there is no known synthetic pathway, and/or an existing pathway needs improvement. Intermediate precursors, known for synthesizing the target compound, may be initially selected and may be progressively transformed into even simpler precursor compounds (e.g., less structurally complex) until only simple or commercially available compounds are required. The goal of retrosynthetic analysis is the structural simplification of the target compound and the discovery of synthetic routes for synthesizing the target compound. In one aspect, a starting material may be a raw material, intermediate, or a drug substance that is used in the production of a drug substance and that is incorporated as a significant structural fragment into the structure of the drug substance.

Interest in synthesizing new chemical compounds and designing feasible reaction pathways is based in part on a multi-industry need for designing compounds with simpler structures to facilitate easier or cheaper synthesis. Manually discovering these reaction pathways is highly laborious and subject to human error.

Moreover, manual retrosynthetic analysis often results in suboptimal reaction pathways having a low success rate (i.e., a success rate for synthesizing a target compound of less than one percent). Computer software for automating the planning reaction pathways is not widely adopted because of high computational costs, which often fails to find successful pathways. In particular, a conventional automated retrosynthesis approach requires exhaustively searching all reaction rules, which can be used to synthesize a target compound (e.g., a reaction rule may split a compound into a simpler precursor compound). For each reaction rule, a set of precursor compounds may be identified, each requiring an exhaustive search until a pathway requiring only simple starting materials is discovered. A complication of this approach arises from the fact that the number of available compounds is ever increasing.

Accordingly, the present invention provides for finding or identifying preferred chemical reaction pathways (e.g., customized, preferred or selected chemical reaction pathways) or non-preferred chemical reaction pathways by a user (e.g., chemist) in order to synthesize a new target designed by the user/chemist. Such personalization contributes to an overall success rate of chemical synthesis. In one aspect, the present invention provides for recommending to a user at least one personalized/customized chemical reaction pathway to synthesize a target molecule. Target compound data of a target compound that a user intends to synthesize may be received. A preference score for one or more chemical reaction pathways to the target compound may be calculated based on one or more chemical reactions. One or more preferred chemical reaction pathways to the targeted compound may be determined using a modified retrosynthetic analysis according to the preference score for one or more chemical reactions.

It should be noted that one or more calculations may be performed using various mathematical operations or functions that may involve one or more mathematical operations (e.g., solving differential equations or partial differential equations analytically or computationally, using addition, subtraction, division, multiplication, standard deviations, means, averages, percentages, statistical modeling using statistical distributions, by finding minimums, maximums or similar thresholds for combined variables, etc.).

Other examples of various aspects of the illustrated embodiments, and corresponding benefits, will be described further herein.

It is understood in advance that although this disclosure includes a detailed description on cloud computing, implementation of the teachings recited herein are not limited to a cloud computing environment and/or computing systems associated with one or more vehicles. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 1:
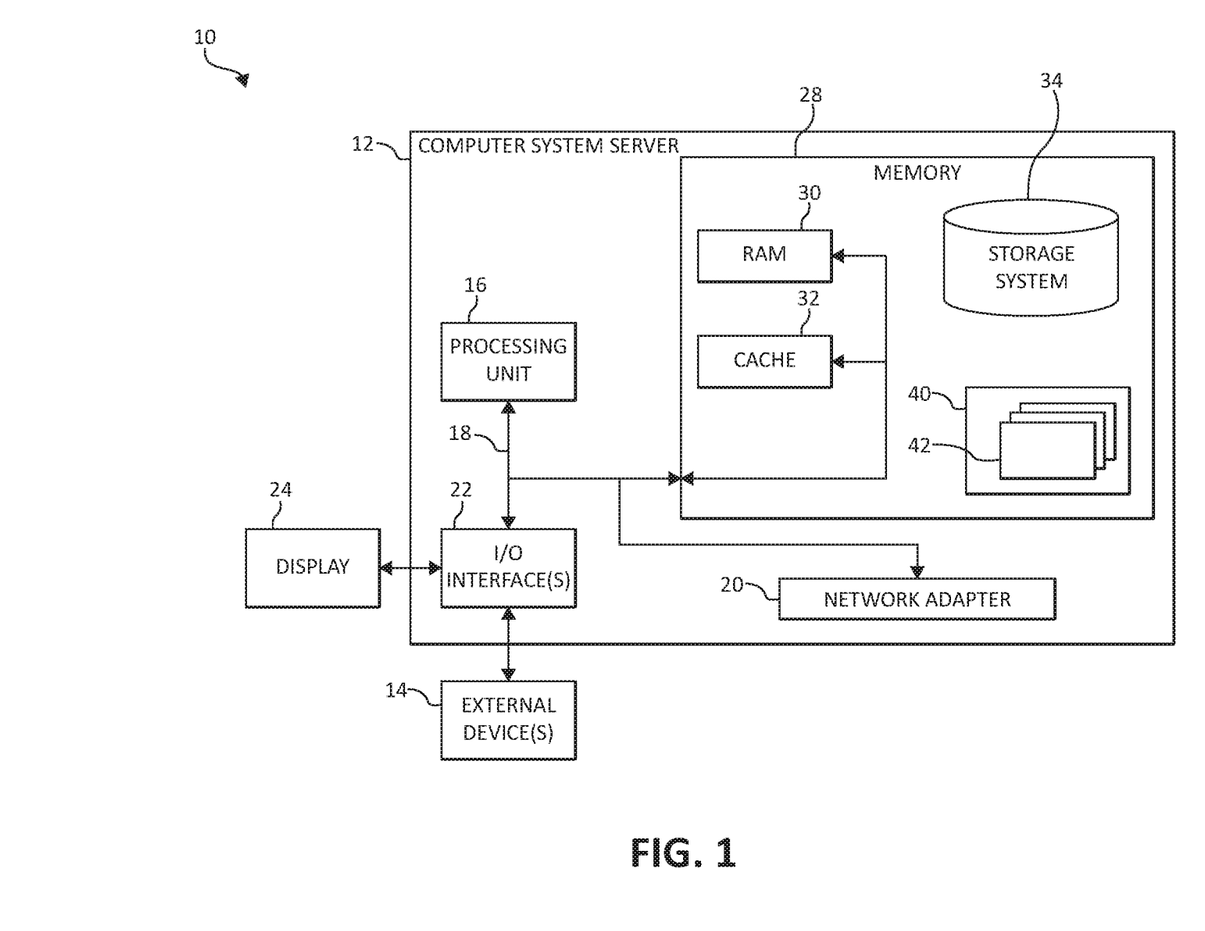
FIG. 1 is a block diagram depicting an exemplary computing node according to an embodiment of the present invention.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, system memory 28 may include at least one program product having a set (e.g., at least one) of program modules that are configured to carry out the functions of embodiments of the invention.

Program/utility 40, having a set (at least one) of program modules 42, may be stored in system memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
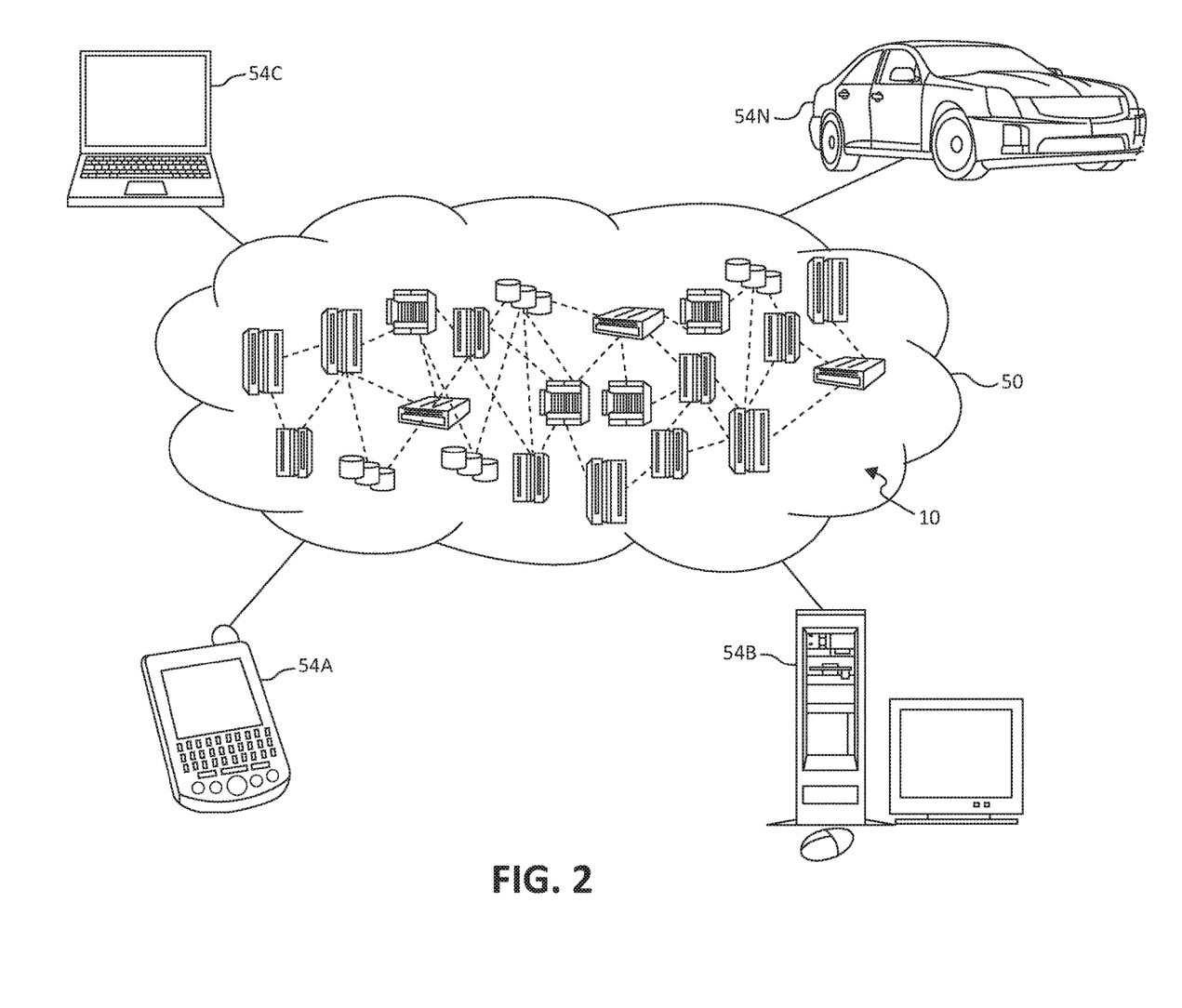
FIG. 2 is an additional block diagram depicting an exemplary cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
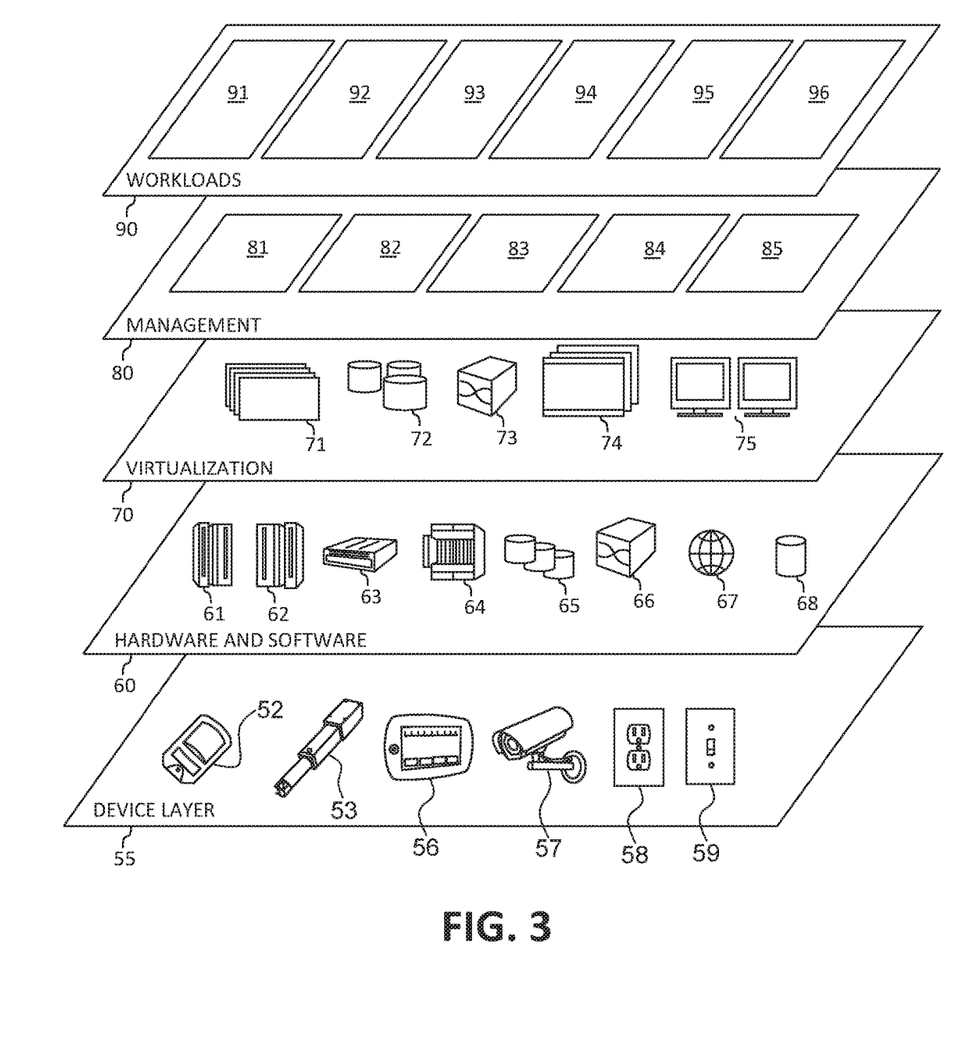
FIG. 3 is an additional block diagram depicting abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Device layer 55 includes physical and/or virtual devices, embedded with and/or standalone electronics, sensors, actuators, and other objects to perform various tasks in a cloud computing environment 50. Each of the devices in the device layer 55 incorporates networking capability to other functional abstraction layers such that information obtained from the devices may be provided thereto, and/or information from the other abstraction layers may be provided to the devices. In one embodiment, the various devices inclusive of the device layer 55 may incorporate a network of entities collectively known as the "internet of things" (IoT). Such a network of entities allows for intercommunication, collection, and dissemination of data to accomplish a great variety of purposes, as one of ordinary skill in the art will appreciate.

Device layer 55 as shown includes sensor 52, actuator 53, "learning" thermostat 56 with integrated processing, sensor, and networking electronics, camera 57, controllable household outlet/receptacle 58, and controllable electrical switch 59 as shown. Other possible devices may include, but are not limited to various additional sensor devices, networking devices, electronics devices (such as a remote-control device), additional actuator devices, so called "smart" appliances such as a refrigerator or washer/dryer, and a wide variety of other possible interconnected objects.

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provides cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and, in the context of the illustrated embodiments of the present invention, various workloads and functions 96 for intelligent discovery of preferred chemical reaction pathways to a synthesized target compound. In addition, workloads and functions 96 for intelligent discovery of preferred chemical reaction pathways to a synthesized target compound may include such operations as data analytics, data analysis, modified retrosynthetic analysis, and as will be further described, notification functionality. One of ordinary skill in the art will appreciate that the workloads and functions 96 for intelligent discovery of preferred chemical reaction pathways to a synthesized target compound may also work in conjunction with other portions of the various abstractions layers, such as those in hardware and software 60, virtualization 70, management 80, and other workloads 90 (such as data analytics processing 94, for example) to accomplish the various purposes of the illustrated embodiments of the present invention.

As previously mentioned, the present invention provides a solution that identifies a chain of chemical reactions that is personalized to the skills of a user and to contextual information (e.g., available starting materials and equipment). In one aspect, the present invention assigns preference scores to various reaction steps (e.g. a positive preference score and/or a negative preference score). The preference scores are used to search for a preferred chemical reaction pathway. The present invention returns to a user at least one preferred chemical reaction pathway, which takes into account a user preference. Accordingly, the present invention may receive, by a processor, target compound data comprising a target compound the user wants to synthesize. The present invention may detect, by a processor, one or more user preferences of reactions using one or more reaction rules for synthesizing the target compound. A chemical reaction pathway may be calculated or determined, by a processor, according the one or more user preferences. A history of the chemical reaction pathways the user preferred and/or non-preferred may be displayed and/or provided.

Thus, the present invention increases the opportuning (e.g., chance) that a chain of chemical reactions returned by the system can be performed outside a computing environment (e.g., practical application) given a specific context (e.g., skills of the user, equipment available, starting materials available, etc.). The present invention may further reduce the rate of failed attempts to synthesize a target molecule.

In one aspect, present invention recommends to a user at least one personalized chemical reaction pathway to synthesize a target molecule. Target compound data of a target compound a user intends to synthesize may be received. A preference score for one or more chemical reaction pathways to the target compound may be calculated based on one or more chemical reactions. One or more preferred chemical reaction pathways to the targeted compound may be determined using a modified retrosynthetic analysis according to the preference score for one or more chemical reactions.

It should be noted, as used herein, a "synthesized target compound" may include a new compound that does not yet exist in the "real world" because nobody has successfully synthesized the new compound. Assuming that a chemist designs a new compound whose reaction pathway is not discovered because that compound has not been successfully synthesized before, the present invention may return a personalized reaction pathway to such a new compound.

Figure 4:
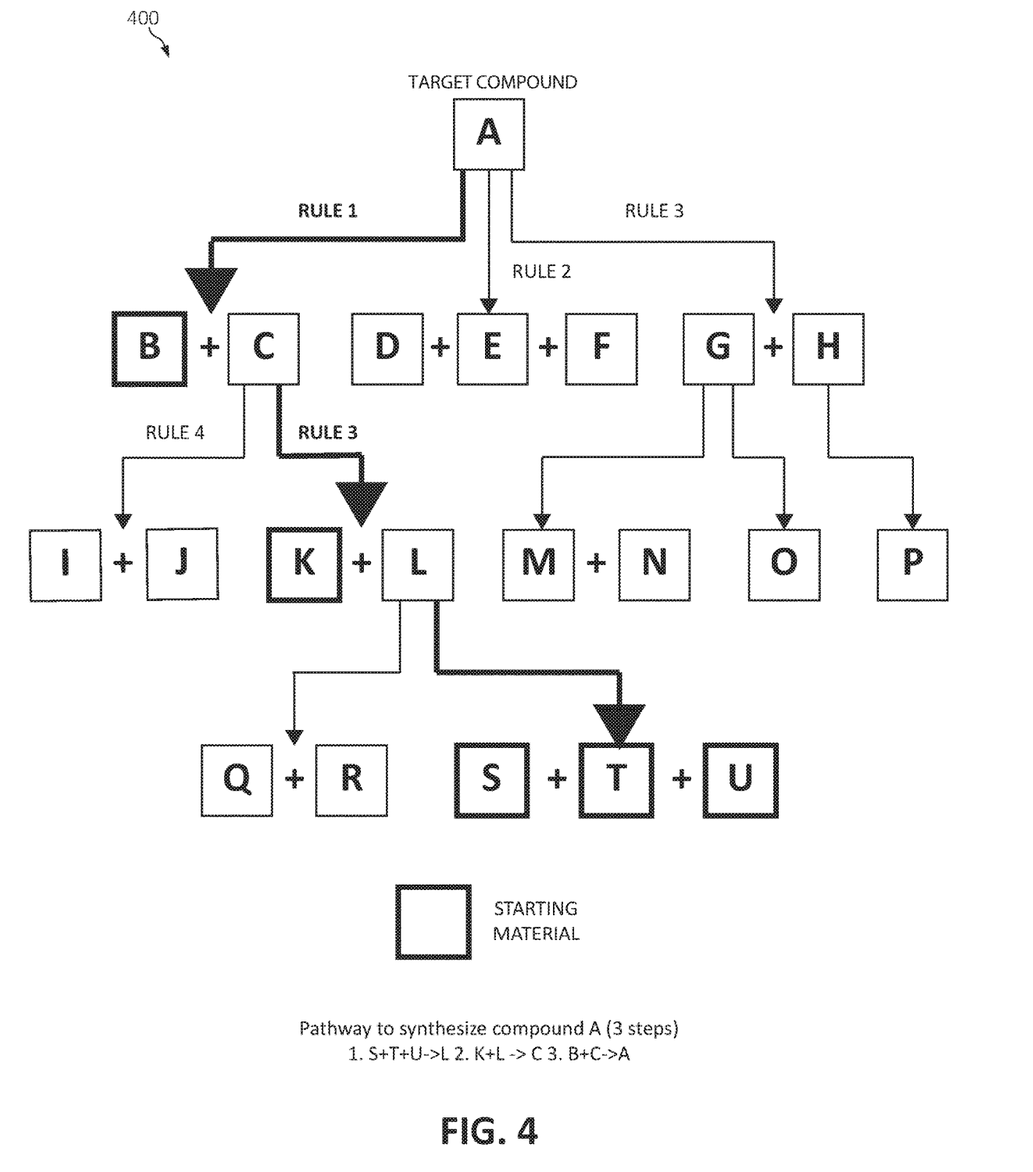
FIG. 4 is an additional block diagram depicting a chemical reaction pathway to a target compound in accordance with aspects of the present invention.

Turning now to FIG. 4, a block diagram 400 depicts a chemical reaction pathway to a target compound to synthesize. As will be seen, many of the functional blocks may also be considered "modules" or "components" of functionality, in the same descriptive sense as has been previously described in FIGS. 1-3. With the foregoing in mind, the module/component blocks 400 may also be incorporated into various hardware and software components of a system for automatic data preprocessing in accordance with the present invention. Many of the functional blocks 400 may execute as background processes on various components, either in distributed computing components, or on a user device, or elsewhere.

As illustrated, FIG. 4 depicts staring with a target compound ("A") to synthesize. Each reaction rule for synthesizing the target compound A, which can be applied to the target compound A, may be identified and/or located such as, for example, rules 1-4. When applying one reaction rule, one or more precursor compounds (e.g., precursor compounds B-U) that may be needed to generate target compound A may also be detected. Each of these operations may be performed, repeated, and/or continue until a starting material needed to synthesize the target compound A is identified and/or determined. Thus, as depicted in FIG. 4, the reaction pathway to synthesize the target compound A is identified in three steps. For example, step 1 indicates that precursor compound S and precursor compound T and precursor compound U yield precursor L. Step 2 indicates that precursor compound K and precursor compound L yield precursor C. Step 3 indicates that precursor compound B and precursor compound C yield the target compound A.

Figure 5:
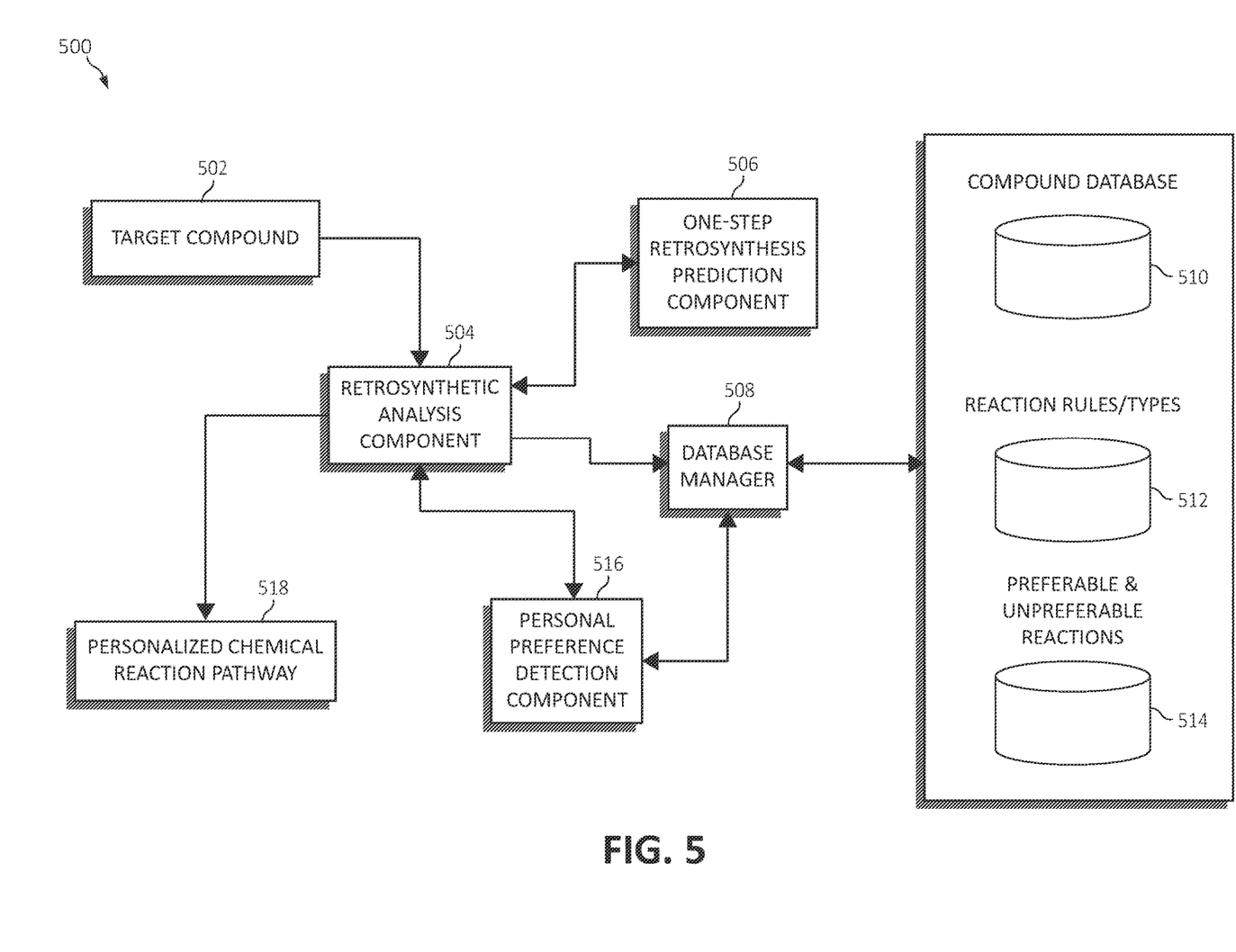
FIG. 5 is an additional block diagram of a processing system for intelligent discovery of preferred chemical reaction pathways to a synthesized target compound in accordance with aspects of the present invention.

Turning now to FIG. 5, a block diagram depicting exemplary functional components 400 according to various mechanisms of the illustrated embodiments is shown. That is, FIG. 5 depicts determining a preferred chemical reaction pathway to a target compound in a computing environment, such as a computing environment 400, according to an example of the present technology. As will be seen, many of the functional blocks may also be considered "modules" or "components" of functionality, in the same descriptive sense as has been previously described in FIGS. 1-3. For example, computer system/server 12 of FIG. 1 may be included in FIG. 5 to execute one or more steps, operations, and/or functions. With the foregoing in mind, the module/component blocks 500 may also be incorporated into various hardware and software components of a system for automatic data preprocessing in accordance with the present invention. Many of the functional blocks 500 may execute as background processes on various components, either in distributed computing components, or on the user device, or elsewhere.

The computing environment 500 may include target compound data 502, a retrosynthetic analysis component 504, a one-step retrosynthesis prediction component 506, a database manager 508, a compound database 510, a reaction rules/types database 512, and/or preferred and non-preferred chemical reactions database 514, and the personal preference detection component 516.

In one aspect, the database manager 508 may provide access to the compound database 510, reaction rules/types database 512, and/or the preferred and non-preferred chemical reactions database 514 for the retrosynthetic analysis component 504 and/or the one-step retrosynthesis prediction component 506. That is, the retrosynthetic analysis component 504 and/or the one-step retrosynthesis prediction component 506 may call upon the compound database 510, reaction rules/types database 512, and/or preferred and non-preferred chemical reactions database 514. The database manager 508 may manage, send, retrieve, or access data stored in each of the compound database 510, reaction rules/types database 512, and/or preferred and non-preferred chemical reactions database 514.

Compound database 510, reaction rules/types database 512, and/or preferred and non-preferred chemical reactions database 514 can include a single database or one or more databases. In some embodiments, the compound database 510, the reaction rules/types database 512, and/or the preferred and non-preferred chemical reactions database 514 may include separate databases. Alternatively, or additionally, the processing system 500 can include dedicated hardware, such as one or more integrated circuits, Application Specific Integrated Circuits (ASICs), Application Specific Special Processors (ASSPs), Field Programmable Gate Arrays (FPGAs), or any combination of the foregoing examples of dedicated hardware for performing the techniques described herein.

In one aspect, the compound database 510 may be populated with known compounds having known properties (e.g., known chemical structures, molecular fingerprints, and/or known synthesis pathways). In some embodiments, the compound database 510 includes partial pathways for one or more compounds.

The database manager 508 may search and/or filter a complete list of compounds stored in the compound database 510. For example, the database manager 508 may search the compound database 510 to determine whether all of the precursors are starting materials. Starting materials are those compounds that are stored in the compound database 510 as commercially available compounds and/or as compounds having known synthesis pathways.

Additionally, the reaction rules/types database 512 may include one or more reaction rules. A reaction rule may split a compound into similar or less-complex precursor compounds. That is, a reaction rule expresses the generation of a compound from precursors. If synthesis is possible using a particular reaction rule, the system applies the reaction rule to generate precursors for the target compound.

The preferred and non-preferred reactions database 514 may include those preferred reactions/reaction pathways (e.g., personal preference reactions of a user) and/or non-preferred reactions/reaction pathways that may be associated with a user. That is, the preferred and non-preferred reactions database 514 may be used for checking, determining, evaluating, and/or identifying those preferred reactions/reaction pathways (e.g., personal preference reactions of a user) and/or non-preferred reactions/reaction pathways of a user. In this way, a recommended reaction may be selected so as to enable a personalized, chemical reaction pathway 518.

The retrosynthetic analysis component 504 may receive a target compound data 502 as input from a client (e.g., as input from a user of the processing system 400 or as input from another system) according to one or more embodiments. The target compound data 502 includes a compound name, a chemical structure, and/or a molecular fingerprint for identifying a target compound. A molecular fingerprint, for example, may be represented by bit strings that summarize molecular information such as, for example, the presence or absence of particular functional groups or combinatorial features.

The retrosynthetic analysis component 504 may provide and/or output one or more preferred chemical reaction pathways 518 to the targeted compound using a retrosynthetic analysis according to the preference score for one or more chemical reactions. That is, the retrosynthetic analysis component 504 may recommend to the user (e.g., chemist scientist) one or more preferred or personalized chemical reaction pathways 518 to the target compound.

The retrosynthetic analysis component 504 may perform a multi-step retrosynthesis until at least one reaction pathway is located and/or identified. Moreover, the retrosynthetic analysis component 504 may internally call and/or access the one-step retrosynthesis prediction component 506 and the personal preference detection component 516. The one-step retrosynthesis prediction component 506 may, given a target compound (e.g., target compound A of FIG. 4) as input, return a set of compounds (e.g., precursor compounds such as those illustrated in FIG. 4), which can synthesize the target compound A in one reaction step. The personal preference detection component 516 may calculate a preference score for one or more chemical reaction pathways to the target compound based on one or more chemical reactions. That is, the preference detection component 516 may, given a set of reactions, return a score of the one-step reaction according to a personal preference of the user.

The retrosynthetic analysis component 504 may determine one or more preferred chemical reaction pathways to the targeted compound using a retrosynthetic analysis according to the preference score for one or more chemical reactions. The retrosynthetic analysis component 504, in conjunction with the personal preference detection component 516, may detect one or more user preferences of the one or more chemical reactions. The retrosynthetic analysis component 504, in conjunction with the personal preference detection component 516, may receive from the preferred and non-preferred reactions database 514 a list of chemical reaction pathways preferred by the user, and/or a list of chemical reaction pathways non-preferred by the user.

The retrosynthetic analysis component 504 may also receive one or more reaction rules from the reaction rule database 512 for determining the one or more preferred chemical reaction pathways and/or one or more reaction types describing a type of reaction for determining the one or more preferred chemical reaction pathways.

The one-step retrosynthesis prediction component 506 may collect feedback relating to the or more preferred chemical reaction pathways, and/or assist with searching for one or more alternative preferred chemical reaction pathways according to the feedback. The one-step retrosynthesis prediction component 506 may be a machine learning operation to predict one or more reactants from one or more products and learn one or more starting materials required for synthesizing the target compound.

Consider for example a scenario ("case 1") using knowledge-based retrosynthetic prediction and a second scenario ("case 2") using a machine learning based retrosynthesis predictions. For example, in case 1, the one-step retrosynthesis prediction component 506 may use the reaction rules/types database 512 and perform one or more operations for pattern matching. Each reaction rule is considered as a template, which represents an important chemical substructure of a product and substructures or complete structures of its reactants. The reaction rule may include additional information, such as reaction temperature, conditions under which the reaction rule cannot be applied, and so on.

In pattern matching, the system checks if a substructure of a compound to synthesize matches that of the product described in that reaction rule. If this is the case, the precursor compounds of that compound are generated according to the reactants in the reaction rule. When the precursor compounds are generated, the substructures of the compound which are not described in the reaction rule remain unchanged. For example, assume that [C:3][C:1](=[O:2])[C:4]>>[C:3][C:1]([O:2])[C:4] is a reaction rule represented in Reaction SMARTS format. The substructure in the right hand side is for the product and the substructure in the left hand side is for a reactant. The number next to an atom indicates a mapping between the product and reactant. In pattern matching using this rule, if a compound to synthesize has the same substructure in the product part, the system generates a precursor compound whose difference from that compound is the bond between a carbon and an oxygen (C=O versus C—O). The remaining substructures are identical between the compound and its precursor compound. The personal preference detection component 516 may determine or check the frequency of each reaction rule, via the reaction rules/type database 512, historically used in reactions a user preferred and/or did not prefer. The personal preference detection component 516 may determine and/or calculate the score of each reaction rule based on the determined frequency used in a reaction. The preference detection component 516 may also consider the user preferences regarding starting materials, purity, price and lead time.

The retrosynthetic analysis component 504 may also determine and provide retrosynthetic analysis and/or perform a graph search. The retrosynthetic analysis component 504 may invoke or call the one-step retrosynthesis prediction component 506 for successor generation. The retrosynthetic analysis component 504 may calculate edge costs of graph by calling the personal preference detection component 516. One embodiment of component 504 is to model retrosynthetic analysis as an "AND/OR" graph search problem. An "OR" node in an AND/OR graph corresponds to one compound, while an AND node corresponds to one or more precursor compounds generated by a reaction rule. The successors of an OR node are AND nodes, and the successors of an AND node are OR nodes. An edge from an OR node to an AND corresponds to applying an applicable reaction rule to a compound in a retrosynthesis manner and generate its precursor compounds. The edge cost in this case is a preference score of that reaction rule. The system assumes that the preference score always has a non-negative value. The smaller the preference score, the stronger the preference. An edge from an AND to an OR node corresponds to selecting one of the precursor compounds for further investigation, and the edge cost in this case is 0. For example, in FIG. 4, OR node "A" representing target compound "A" has three edges "rule 1," "rule 2," and "rule 4", leading to AND node "B+C", AND node "D+E+F", and AND node "G+H", respectively. The AND node "B+C" has two edges (not shown explicitly in FIG. 4) leading to respectively OR node "B" which is a starting material, and OR node "C" which has two AND nodes "I+J" and "K+L". At an OR node corresponding to a compound, the system attempts to find one edge (reaction rule) which guarantees that that compound is proven to be synthesized. At an AND node corresponding to a set of precursor compounds, the system attempts to prove that all of these precursor compounds can be synthesized. The initial AND/OR graph contains only a root OR node which corresponds to the target compound. The AND/OR graph search gradually grows in the size of the graph as necessary by expanding nodes with applicable reaction rules and propagating back preference scores, until finding a so-called solution tree which represents a reaction pathway to synthesize the target compound. Optimally, the AND/OR graph may perform a search such as, for example, AO* and RBFAOO, can find an optimal solution tree which includes a reaction pathway with the best preference score. The preference score of a reaction pathway is calculated by the sum of the edge costs in its solution tree.

In case 2, for the machine learning based retrosynthesis prediction, the one-step retrosynthesis prediction component 506 may use a neural network model (e.g., a neural sequence-to-sequence model). The one-step retrosynthesis prediction component 506 may use one or more reaction types, stored in the reaction rules/types database 512, such as, for example, Carbon-Carbon bond formation, oxidation, reduction, etc.

The personal preference detection component 516 may extract a reaction core in each step of reactions the user historically preferred and/or did not prefer. The personal preference detection component 516 may calculate the frequency of each reaction core. When one-step reaction prediction is performed by the one-step retrosynthesis prediction component 506, personal preference detection component 516 may check a reaction core and return a score based on the frequency of the reaction core.

The retrosynthetic analysis component 504 may perform the various functions and operations as described in case 1.

It should be noted that if one or more chemical reactions that a user performed previously are available, the present may receive them as input. Also, the reactions the user prefers and/or does not prefer can be accumulated and stored in the preferred and non-preferred reactions, by monitoring and checking the actions of the user and/or by collecting user feedback. Also, a recommended reaction may be selected. One or more user reactions preferences may be received via a graphical user interface ("GUI"), which enables for personalize pathways even if no preferred reactions are available.

The preferred reactions the user may be learn due to frequency of use (e.g., popularity) and may be recommended to the user. For example, let "P" be a pathway recommended to the user taking into account the reaction preferences of the user. A scoring function "F" may calculates the edge costs based on the reactions preferred by all the users. A retrosynthetic analysis may be performed to find a pathway "Q" using scoring function "F." The preference score of pathway P may be determined using scoring function "F." If preference score of pathway P is less than a selected threshold and/or is less than/or greater than that of pathway Q (e.g., pathway P is less efficient than pathway Q), the pathway Q may be recommend to the user as a preferred chemical reaction pathway to the targeted compound (in addition to pathway P).

The personal preference detection component 516 may be a required part of the retrosynthetic analysis to efficiently obtain an optimal solution (e.g., one or more personalized and preferred chemical reaction pathways to the targeted compound using a retrosynthetic analysis). For example, let "b" be a number of reaction rules, "p" be a number of precursor compounds generated by one reaction rule, and "d" be a search depth to starting materials, which is defined as the number of reaction rules applied from the target compound to reach the starting materials. That is, the search depth may be the length of the path (number of edges) from a root node of the search to the current node. In order to find "O" that is an optimal personalized pathway, the present invention attempts to perform a search as similar to a theoretically minimum search space of (e.g., $O(p^{\wedge}(d/2))$ by guiding a search with the personalized scores.

Figure 6:
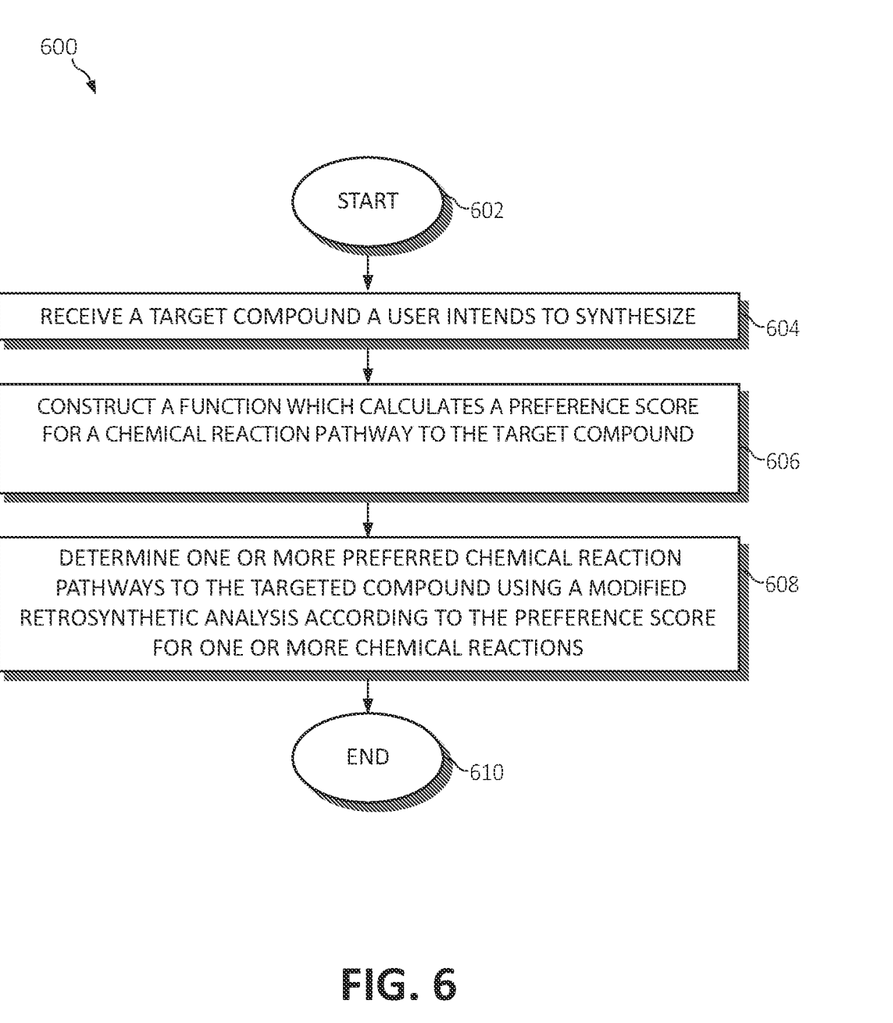
FIG. 6 is a flowchart diagram depicting an exemplary method for intelligent discovery of preferred chemical reaction pathways to a synthesized target compound in accordance with aspects of the present invention.

Turning now to FIG. 6, a method 600 for intelligent discovery of preferred chemical reaction pathways to a synthesized target compound by a processor is depicted, in which various aspects of the illustrated embodiments may be implemented. In one aspect, FIGS. 1-5 may be used herein to perform one or more functions, features, and/or operations of FIG. 6. The functionality 600 may be implemented as a method executed as instructions on a machine, where the instructions are included on at least one computer readable medium or one non-transitory machine-readable storage medium. The functionality 600 may start in block 602.

A target compound data of a target compound that a user intends to synthesize may be received, as in block 604. A function which calculates a preference score for a chemical reaction pathway to the target compound may be constructed based on one or more chemical reactions in the preferable/unpreferable reactions database, as in block 606.

The constructed function is used in block 608 to calculate a preference score of a reaction pathway found by a modified retrosynthetic analysis. One or more preferred chemical reaction pathways to the targeted compound may be determined using a retrosynthetic analysis according to the preference score for one or more chemical reactions as in block 608. The functionality 600 may end, as in block 610.

Figure 7:
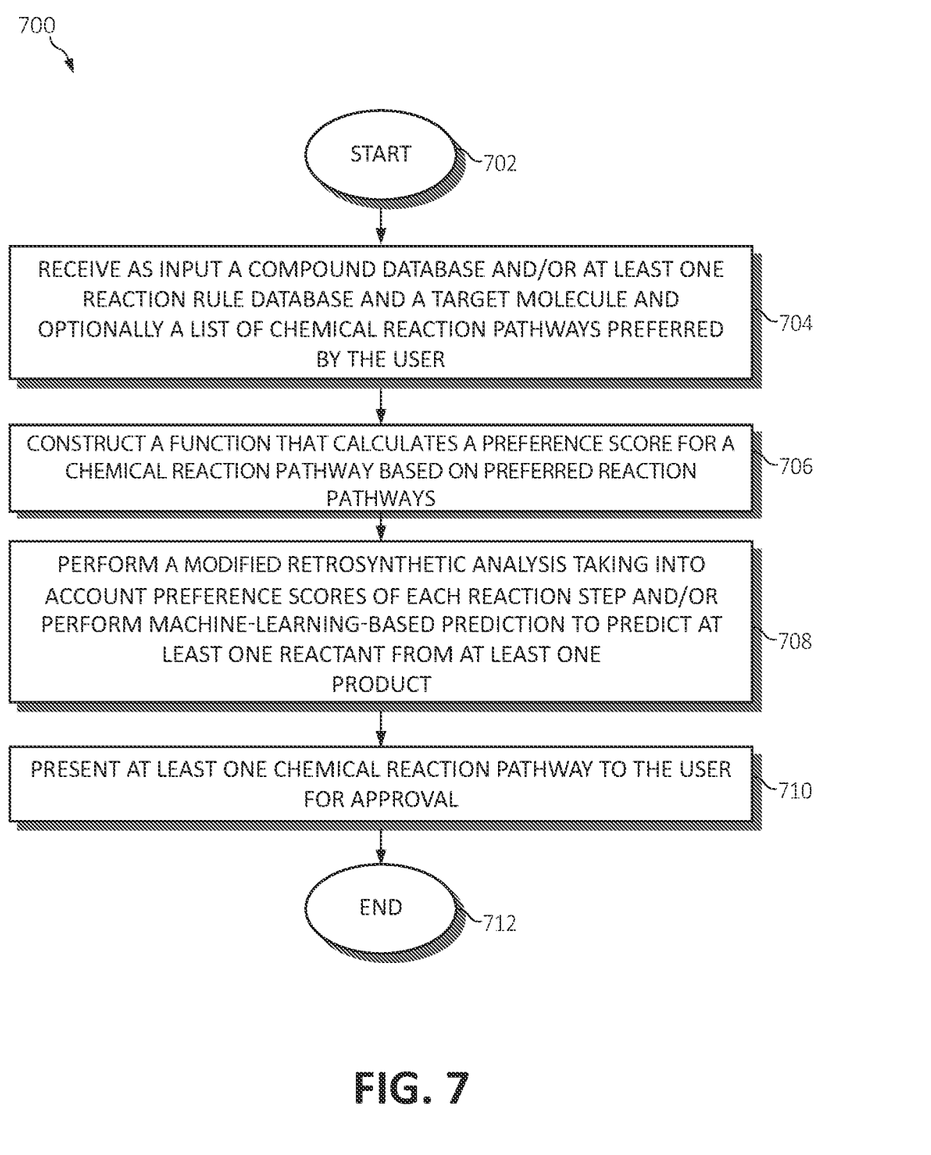
FIG. 7 is a flowchart diagram depicting an additional exemplary method for intelligent discovery of preferred chemical reaction pathways to a synthesized target compound by a processor, again in which aspects of the present invention may be realized.

Turning now to FIG. 7, a method 700 for intelligent discovery of preferred chemical reaction pathways to a synthesized target compound by a processor is depicted, in which various aspects of the illustrated embodiments may be implemented. In one aspect, FIGS. 1-5 may be used herein to perform one or more functions, features, and/or operations of FIG. 7. The functionality 700 may be implemented as a method executed as instructions on a machine, where the instructions are included on at least one computer readable medium or one non-transitory machine-readable storage medium. The functionality 700 may start in block 702.

Target compound data of a target compound, selected data from a compound database and/or at least one reaction rule database, a list of chemical reaction pathways preferred by the user, or a combination thereof may be received as input, as in block 704. A function which calculates a preference score of a reaction pathways may be constructed based on preferred reaction pathways, as in block 706. The constructed function is used in block 708 to calculate a preference score of a reaction pathway found by a modified retrosynthetic analysis. A retrosynthetic analysis may be performed while considering and taking into account each preference score of each reaction step and/or a machine-learning-based prediction that may be performed to predict at least one reactant from at least one product/compound, as in block 708. At least one chemical reaction pathway (e.g., a customized, preferred, and/or personalized chemical reaction pathway 518 of FIG. 5) may be presented or provided to the user for approval, as in block 710. The functionality 700 may end, as in block 712.

In one aspect, in conjunction with and/or as part of at least one block of FIGS. 6-7, the operations of methods 600 and 700 may include each of the following. The operations of methods 600 and 700 may also detect one or more user preferences of the one or more chemical reactions.

The operations of methods 600 and 70 may receive a list of chemical reaction pathways preferred by the user; or receive a list of chemical reaction pathways non-preferred by the user. The operations of methods 600 and 700 may receive one or more reaction rules from a reaction rule database for determining the one or more preferred chemical reaction pathways; and/or receive one or more reaction types describing a type of reaction for determining the one or more preferred chemical reaction pathways. Feedback may be collected relating to the or more preferred chemical reaction pathways. Also, one or more alternative preferred chemical reaction pathways may be determined according to the feedback. The operations of methods 600 and 700 may initialize a machine learning operation to predict one or more reactants from one or more products and/or may provide the one or more preferred chemical reaction pathways in an interactive GUI.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowcharts and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowcharts and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowcharts and/or block diagram block or blocks.

The flowcharts and block diagrams in the Figures illustrate the architecture, functionality, and operation of possible implementations of systems, methods, and computer program products according to various embodiments of the present invention. In this regard, each block in the flowcharts or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts or carry out combinations of special purpose hardware and computer instructions.

The invention claimed is:

1. A method for intelligent discovery of preferred chemical reaction pathways to a synthesized target compound in a computing environment by a processor, comprising:
   receiving, by the processor, target compound data of a target compound a user intends to synthesize;
   calculating, by the processor using at least one of a node graph searching operation and a machine learning operation, a preference score for one or more chemical reaction pathways to the target compound based on one or more chemical reactions, wherein the preference score is personalized to a skill level of the user and calculated based on detected preferences of the user, the detected preferences inclusive of starting materials and equipment available to the user to synthesize the target compound;
   determining, by the processor as an output of the at least one of the node graph searching operation and the machine learning operation, one or more preferred chemical reaction pathways to synthesize the target compound using a modified retrosynthetic analysis according to the preference score for one or more chemical reactions, wherein, given input of the target compound, the determination of precursor compounds of the one or more preferred chemical reaction pathways to synthesize the target compound are returned as the output in one reaction step; and
   displaying, by the processor via an interactive graphical user interface (GUI), the one or more preferred chemical reaction pathways to the target compound listed in an order based on the preference score for the one or more chemical reactions.

2. The method of claim 1, further including:
   receiving a list of chemical reaction pathways preferred by the user; or
   receiving a list of chemical reaction pathways non-preferred by the user.

3. The method of claim 1, further including:
   receiving one or more reaction rules from a reaction rule database for determining the one or more preferred chemical reaction pathways; or
   receiving one or more reaction types describing a type of reaction for determining the one or more preferred chemical reaction pathways.

4. The method of claim 1, further including:
   collecting feedback relating to the or more preferred chemical reaction pathways; or
   searching for one or more alternative preferred chemical reaction pathways according to the feedback.

5. The method of claim 1, further including initializing a machine learning operation to predict one or more reactants from one or more products and learn one or more starting materials required for synthesizing the target compound.

6. A system for intelligent discovery of preferred chemical reaction pathways to a synthesized target compound, comprising:
   one or more computers with executable instructions that when executed by a processor cause the system to:
   receive, by the processor, target compound data of a target compound a user intends to synthesize;
   calculate, by the processor using at least one of a node graph searching operation and a machine learning operation, a preference score for one or more chemical reaction pathways to the target compound based on one or more chemical reactions, wherein the preference score is personalized to a skill level of the user and calculated based on detected preferences of the user, the detected preferences inclusive of starting materials and equipment available to the user to synthesize the target compound;
   determine, by the processor as an output of the at least one of the node graph searching operation and the machine learning operation, one or more preferred chemical reaction pathways to synthesize the target compound using a modified retrosynthetic analysis according to the preference score for one or more chemical reactions, wherein, given input of the target compound, the determination of precursor compounds of the one or more preferred chemical reaction pathways to synthesize the target compound are returned as the output in one reaction step; and
   display, by the processor via an interactive graphical user interface (GUI), the one or more preferred chemical reaction pathways to the target compound listed in an order based on the preference score for the one or more chemical reactions.

7. The system of claim 6, wherein the executable instructions further:
   receive a list of chemical reaction pathways preferred by the user; or
   receive a list of chemical reaction pathways non-preferred by the user.

8. The system of claim 6, wherein the executable instructions further:
   receive one or more reaction rules from a reaction rule database for determining the one or more preferred chemical reaction pathways; and
   receive one or more reaction types describing a type of reaction for determining the one or more preferred chemical reaction pathways.

9. The system of claim 6, wherein the executable instructions further:
   collect feedback relating to the or more preferred chemical reaction pathways; or
   search for one or more alternative preferred chemical reaction pathways according to the feedback.

10. The system of claim 6, wherein the executable instructions further initialize a machine learning operation to predict one or more reactants from one or more products and learn one or more starting materials required for synthesizing the target compound.

11. A computer program product for intelligent discovery of preferred chemical reaction pathways to a synthesized target compound by a processor, the computer program product comprising a non-transitory computer-readable storage medium having computer-readable program code portions stored therein, the computer-readable program code portions comprising:
   an executable portion that receives, by the processor, target compound data of a target compound a user intends to synthesize;
   an executable portion that calculates, by the processor using at least one of a node graph searching operation and a machine learning operation, a preference score for one or more chemical reaction pathways to the target compound based on one or more chemical reactions, wherein the preference score is personalized to a skill level of the user and calculated based on detected preferences of the user, the detected preferences inclusive of starting materials and equipment available to the user to synthesize the target compound;

an executable portion that determines, by the processor as an output of the at least one of the node graph searching operation and the machine learning operation, one or more preferred chemical reaction pathways to synthesize the target compound using a modified retrosynthetic analysis according to the preference score for one or more chemical reactions, wherein, given input of the target compound, the determination of precursor compounds of the one or more preferred chemical reaction pathways to synthesize the target compound are returned as the output in one reaction step; and an executable portion that displays, by the processor via an interactive graphical user interface (GUI), the one or more preferred chemical reaction pathways to the target compound listed in an order based on the preference score for the one or more chemical reactions.

12. The computer program product of claim 11, wherein the executable portion that:

receives a list of chemical reaction pathways preferred by the user;

receives a list of chemical reaction pathways non-preferred by the user;

receives one or more reaction rules from a reaction rule database for determining the one or more preferred chemical reaction pathways; or receive one or more reaction types describing a type of reaction for determining the one or more preferred chemical reaction pathways.

13. The computer program product of claim 11, wherein the executable portion that:

collects feedback relating to the or more preferred chemical reaction pathways; or searches for one or more alternative preferred chemical reaction pathways according to the feedback.

14. The computer program product of claim 11, wherein the executable portion that initializes a machine learning operation to predict one or more reactants from one or more products and learn one or more starting materials required for synthesizing the target compound.

* * * * *